US00PP29390P3

(12) United States Plant Patent
Schoone

(10) Patent No.: US PP29,390 P3
(45) Date of Patent: Jun. 12, 2018

(54) ***PHALAENOPSIS* ORCHID PLANT NAMED 'ELASTIC LOVE'**

(50) Latin Name: *Phalaenopsis hybrida*
Varietal Denomination: Elastic Love

(71) Applicant: Floricultura, Heemskerk (NL)

(72) Inventor: René Schoone, Assendelft (NL)

(73) Assignee: Floricultura, Heemskerk (NL)

( * ) Notice: Subject to any disclaimer, the term of this patent is extended or adjusted under 35 U.S.C. 154(b) by 0 days. days.

(21) Appl. No.: 15/330,458

(22) Filed: Sep. 23, 2016

(65) Prior Publication Data

US 2017/0094867 P1 Mar. 30, 2017

Related U.S. Application Data

(60) Provisional application No. 62/232,208, filed on Sep. 24, 2015.

(51) Int. Cl.
*A01H 5/02* (2018.01)

(52) U.S. Cl.
USPC ..... Plt./311

(58) Field of Classification Search
USPC ..... Plt./263.1, 311
See application file for complete search history.

*Primary Examiner* — Susan McCormick Ewoldt
*Assistant Examiner* — Karen M Redden
(74) *Attorney, Agent, or Firm* — Sunit Talapatra; Foley & Lardner LLP

(57) ABSTRACT

A new and distinct *Phalaenopsis* plant named 'Elastic Love' particularly characterized by flowers which are red/purple with a darker red/purple labellum; plants which may be propagated economically and uniformly using tissue culture; plants which produce more than one inflorescence; long and sturdy inflorescences; and relatively short, dark-green foliage.

3 Drawing Sheets

Latin name of the genus and species of the plant claimed: *Phalaenopsis hybrida.*

Variety denomination: 'Elastic Love'.

BACKGROUND OF THE INVENTION

The present invention relates to a new and distinct cultivar of *Phalaenopsis* plant, botanically known as *Phalaenopsis* of the Orchidaceae family, and hereinafter referred to by the cultivar name 'Elastic Love'.

*Phalaenopsis* comprises a genus of about 55 species of herbaceous perennials many of which, or the hybrids thereof, are suitable for cultivation in the home or greenhouse. *Phalaenopsis* is predominantly epiphytic or rock-dwelling, and is native to tropical Asia, the Malay Archipelago, and Oceania. The species typically has 2-ranked, fleshy, oblong or elliptic leaves affixed to a short central stem (monopodial growth), which vary in size from 5 to 8 inches to over 2 feet. The leaves may be entirely green or mottled with silver grey.

*Phalaenopsis* orchids, often referred to as 'Moth Orchids' in the horticultural trade, are frequently used to furnish cut flowers for the florist trade or sold as flowering potted-plants for home or interiorscape.

*Phalaenopsis* produces upright or pendent lateral racemes, often with many showy flowers which open in succession beginning with the lowermost. The flowers possess three sepals and three petals; the lateral ones being alike. The lowermost petal, called the labellum, is three-lobed and is often more brightly-colored than the other flower segments. Flower colors include various shades of pink, white, yellow and red-brown.

*Phalaenopsis* orchids are typically propagated from seeds. Asexual propagation of *Phalaenopsis* is often done from off-shoots which frequently arise from the lower bracts of the inflorescence. The resulting plants are detached from the mother plant and may be planted in a suitable substrate.

The new *Phalaenopsis* 'Elastic Love' is a product of a controlled breeding program conducted by the inventor, René Schoone, in Strengweg, Heemskerk, The Netherlands. The objective of the breeding program was to develop a new *Phalaenopsis* cultivar particularly characterized by its attractive and unique colored flowers, economical propagation via tissue culture, rapid growth, and a plant dimension suitable for packaging and shipping to the market.

The new *Phalaenopsis* 'Elastic Love' originated from a cross made by the inventor in 2003 in Strengweg, Heemskerk, The Netherlands. The female or seed parent is the *Phalaenopsis* cultivar designated 'Yu Pin Royal', unpatented. The male or pollen parent is the *Phalaenopsis* cultivar designated 'Maki Watanebe', unpatented. The new *Phalaenopsis* 'Elastic Love' was discovered and selected by the inventor as a single flowering plant within the progeny of the stated cross in a controlled environment in 2011 in Strengweg, Heemskerk, The Netherlands.

Asexual reproduction of the new *Phalaenopsis* cultivar by tissue culture (mericloning) was first performed in November, 2010 in Cieweg 13, Heemskerk, The Netherlands, and has demonstrated that the combination of characteristics as herein disclosed for the new cultivar are firmly fixed and retained through successive generations of asexual reproduction. The new cultivar asexually reproduces true-to-type.

BRIEF DESCRIPTION OF THE INVENTION

The following traits have been repeatedly observed and are determined to be unique characteristics of 'Elastic Love', which in combination distinguish this *Phalaenopsis* as a new and distinct cultivar:

1. flowers which are red/purple with a darker red/purple labellum;
2. plant produces more than one inflorescence;
3. plants may be propagated economically and uniformly using tissue culture;
4. inflorescences are long and sturdy; and
5. relatively short, dark-green foliage.

In comparison with the parental cultivars of 'Elastic Love', the flowers of the female parent 'Yu Pin Royal' are larger than the flowers of 'Elastic Love' and dark pink/purple in color. The flowers of the male parent 'Maki Watanebe' are smaller than the flower of 'Elastic Love' and the color is white with some pink purple/violet, whereas the flowers of 'Elastic Love' are red/purple.

Presently, the commercial cultivar to which 'Elastic Love' can be meaningfully compared is '334104' (not patented). 'Elastic Love' is a little lighter in color and the flowers are a little smaller than '334104' (not patented).

BRIEF DESCRIPTION OF THE PHOTOGRAPHS

The accompanying photographs illustrate the overall appearance of the new *Phalaenopsis* 'Elastic Love' showing the colors as true as is reasonably possible with colored reproductions of this type. Colors in the photographs may differ slightly from the color values cited in the detailed botanical description, which accurately describe the color of 'Elastic Love'.

DETAILED BOTANICAL DESCRIPTION

Figure 1:
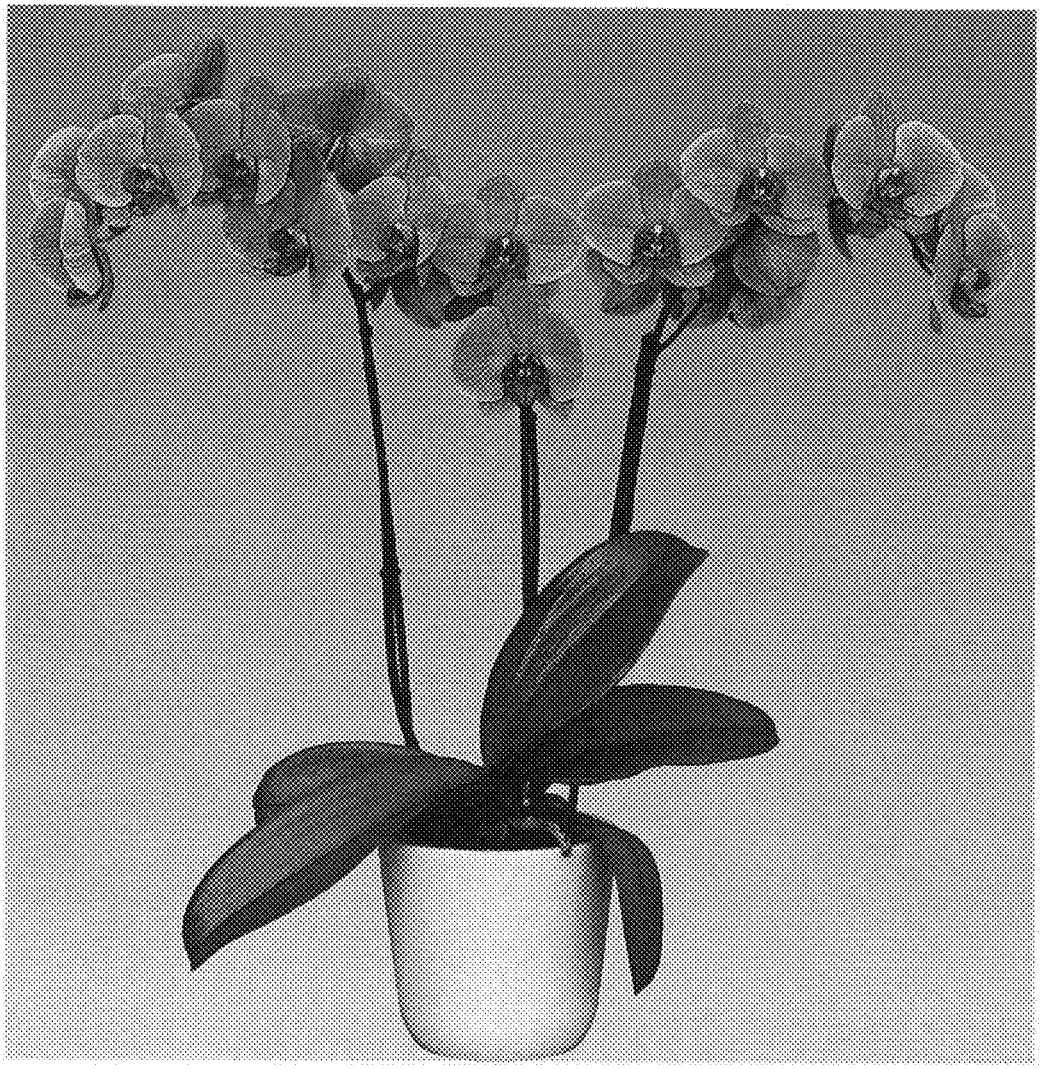
FIG. 1 shows a side view perspective of a typical flowering plant of 'Elastic Love' in a 12 cm pot, at 16 months of age.

The new *Phalaenopsis* cultivar 'Elastic Love' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe plants of 'Elastic Love' as grown in a greenhouse in Strengweg, Heemskerk, The Netherlands, under conditions which closely approximate those generally used in commercial practice. Initially, the ideal temperature to grow plants of 'Elastic Love' is 27° C. during the day and at night. Then, during the flowering phase of 'Elastic Love', the ideal growing temperature is 20-22° C. during the day and 18° C. at night. Light levels for growing 'Elastic Love' are a minimum of 5,000 lux and a maximum of 10,000 lux. A balanced fertilizer with level of 200 ppm N, 87 ppm P, 168 ppm K is applied. Duration of growth of 'Elastic Love' from potting size is between 10 and 14 months.

Color references are made to The Royal Horticultural Society Colour Chart (R.H.S.), 2007 edition, except where general colors of ordinary significance are used. Color values were taken under daylight conditions at approximately noon in Zaandammerweg, Assendelft, The Netherlands. The age of the 'Elastic Love' plants described is 12 months after potting.

Classification:

*Botanical.*—*Phalaenopsis hybrida.*

Parentage:

*Female or seed parent.*—*Phalaenopsis* cultivar designated 'Yu Pin Royal', unpatented.

*Male or pollen parent.*—*Phalaenopsis* cultivar designated 'Maki Watanebe', unpatented.

Propagation:

*Type.*—Tissue culture.

*Rooting habit and description.*—Fleshy; approximately 3 mm-8 mm wide and greyed/green in color (RHS 188A); freely branching. It takes 12 weeks for plants growing in tissue culture to initiate roots.

Plant:

*Size at maturity.*—Height (from bottom of pot to highest flower): about 60-70 cm. Spread: about 35 to 70 cm.

*Growth habit.*—Standard; green leaves (RHS N137A) and a relatively normal raceme.

*Vigor.*—Moderate.

*Crop time.*—Following asexual propagation, at about 26 weeks 2 leaves appear; at about 30 weeks 3-4 leaves appear; after a cold treatment of about 4-8 weeks at a temperature of about 19° C. about 1-3 racemes with flowers appear.

Foliage:

*Quantity per plant.*—About 6-8 leaves are produced before flowering.

*Arrangement and attachment.*—Half up/horizontal and on two sides.

*Overall shape of leaf.*—Oval; the tip is blunt and asymmetric.

*Texture* (*upper & underside*).—Smooth and leathery.

*Pubescence.*—None.

*Mature leaf length.*—About 20 cm.

*Mature leaf width.*—About 8 cm.

*Mature leaf thickness.*—About 2 mm.

*Mature leaf color.*—Upper side: green (RHS N137A). Under side: green (RHS 137A) with greyed/purple (RHS 187A).

*Leaf base.*—Acute.

*Margin.*—Entire.

*Venation.*—Pattern: parallel. Color of midvein: upper side: green (RHS 139A). Under side: greyed/purple (RHS 187A).

Inflorescence description:

*Appearance.*—Upright to slightly pendant, racemose inflorescence with bilaterally symmetrical flowers that open in succession beginning with the lowermost flower.

Raceme:

*Quantity per plant.*—About 1 to 3.

*Number of flowers per raceme.*—About 5-12.

*Length.*—About 20 cm.

*Diameter.*—About 10 cm.

Peduncle:

*Length.*—About 40 cm.

*Diameter.*—About 4 mm.

*Strength.*—Strong.

*Aspect.*—Upright.

*Texture.*—Glabrous and smooth.

*Color.*—Brown (RHS 200A) with green (RHS 137A).

Buds:

*Height* (*from base to tip*).—About 22 mm.

*Diameter* (*at midpoint*).—About 17 mm.

*Shape.*—Oval with a bump.

*Color*.—Red/purple (RHS 59A) with yellow/green (RHS 144C).

*Orientation*.—Same as flowers (forward facing).

*Flowering time*.—For an untreated plant (flowering plant that has not undergone cold-treatment where the plant grows at a temperature of 18° C. to 19° C. for about 4 to 8 weeks after a period of about 30 weeks at a temperature of 25° C.), 1-3 racemes appear with flower buds and flowers. First flowers can be expected approximately 4 to 6 months after planting a plant with a leaf diameter of 3 to 5 cm. Flowers persistent.

*Flowering longevity*.—On the plant: about 4 to 6 months; lastingness of cut flowers: has not been observed.

*Fragrance*.—No fragrance.

Figure 2:
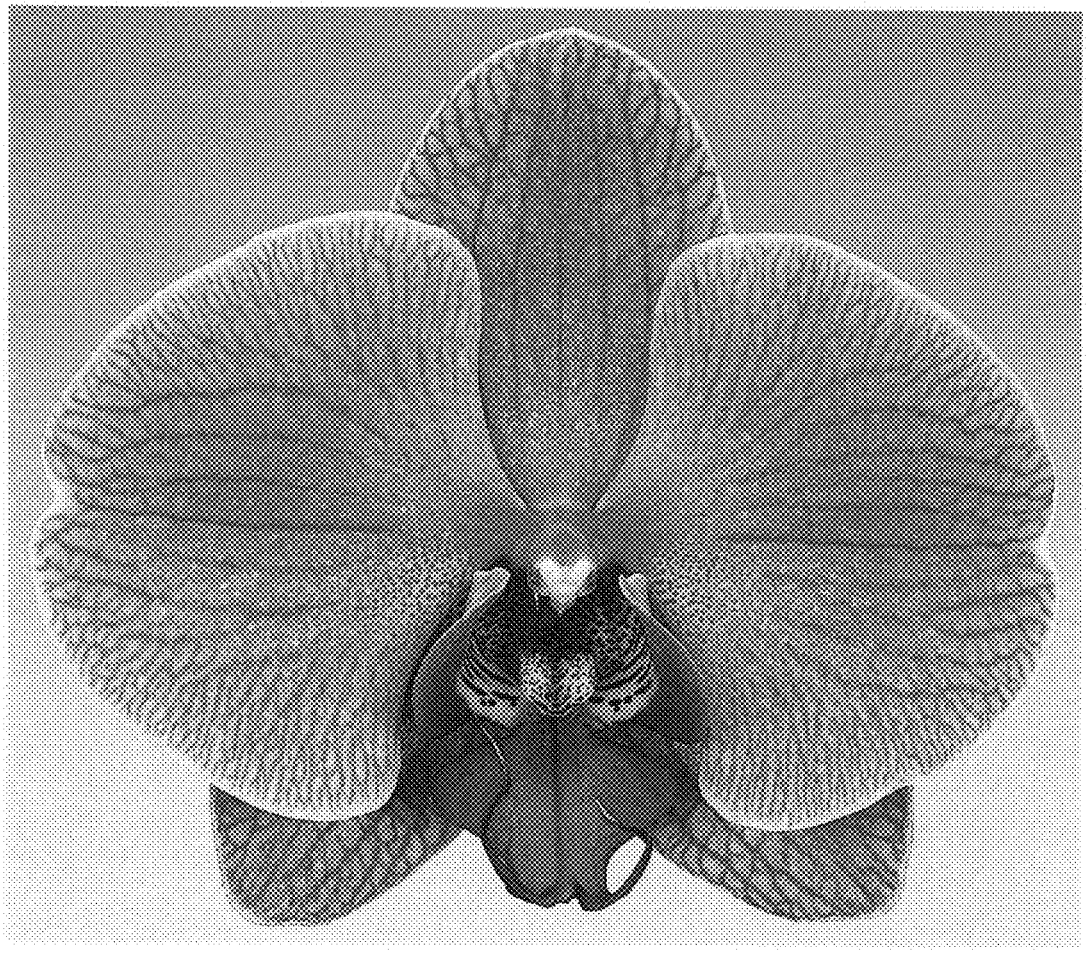
FIG. 2 shows a close-up view of the typical flower of 'Elastic Love', at 16 months of age.
Figure 3:
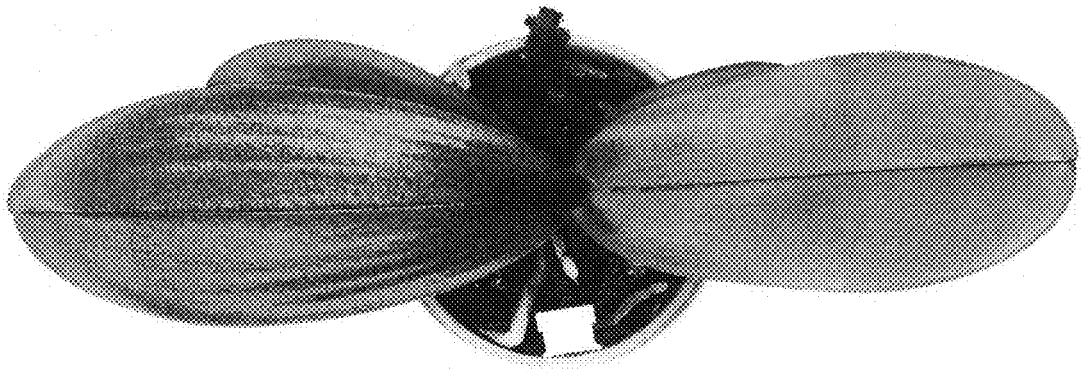
FIG. 3 shows a close-up view of the typical leaves of 'Elastic Love', at about 60 weeks of age.

*Flower*.—Rate of opening: Flowers fully opened about 2 to 3 days after petal and sepal separation. Orientation at opening: slanted upward and outward. Shape: Typical shape of *Phalaenopsis*; see FIG. 2. Size (of single bloom): Height: about 85 mm. Diameter: about 95 mm. Quantity and arrangement: three petals and three sepals that are trimerous, overlapping and arranged in 2 whorls. Petals are more pronounced than sepals.

*Petals*.—Arrangement: Inner whorl comprises 3 petals: 2 lateral petals and a labellum. 2 lateral petals: Overall shape: broadly ovate and weakly cupped. Apex: round with a notch. Margin: entire and weakly undulate. Base: broadly ovate. Length: about 55 mm. Width: about 45 mm. Texture: Upper surface: smooth and satiny. Under surface: smooth and satiny. Color (when fully opened): upper side: red/purple (RHS 72B) with red/purple stripes (RHS 72A). On the edges a haze of white (RHS NN155C). At the base some white (RHS NN155C) with red/purple spots (RHS 72A). Under side: purple (RHS 77B) with a white haze (RHS NN155C). Color (when first opened): red/purple (RHS 72B) with red/purple stripes (RHS 72A. At the base some white (RHS NN155C) with red/purple spots (RHS 72A) and a yellow/green haze (RHS 146D). Labellum: Overall shape: 3-lobed with 2 prominent callosities at central junction of the lateral lobes and base of the midlobe. Lateral lobes of labellum fold upward about the column; the midlobe extends forward and is terminated by 2 filiform appendages at the apex. Lateral lobes of the labellum are ovate in shape while the midlobe is triangular with a bump and a rib on it. Margin: entire and weakly undulate. Apex of the mid lobe and lateral lobes: oval. Length mid lobe: about 22 mm. Width mid lobe (not flattened): about 25 mm. Length lateral lobe: about 22 mm. Width lateral lobe (not flattened): about 16 mm. Depth of tube created by lateral lobes of labellum: about 22 mm. Texture: Upper & under surface: smooth and satiny. Color (when fully opened): Midlobe, upper side: main color is red/purple (RHS 71A) with at the corners some greyed/red (RHS 178A) and at the mid vein red/purple (RHS 59A). Under side: main color is red/purple (RHS 70A) with at the corners some greyed/red (RHS 178A). Lateral lobes, upper side: at the base white (RHS NN155C) with red/purple stripes/spots (RHS 71A). Upper edge red/purple (RHS 70A) and lower edge red/purple (RHS 70A) with a haze of greyed/red (RHS 178A). Under side: main color is red/purple (RHS 70A) from the base some white (RHS NN155C) with a haze of grey/red (RHS 178A). Cirrhi: about 20 mm. Color: red/purple (RHS 71A) with white tips (RHS NN155C). Pestle (Callosities): Length: about 9 mm. Width (not flattened): about 7 mm. Color: yellow (RHS 7A) with red/purple stripes and spots (RHS 71A).

*Sepals*.—Arrangement: Outer whorl comprises 3 sepals, one dorsal and two lateral sepals. Overall shape: elliptical and weakly cupped. Margin: entire and weakly undulate. Length: about 45 mm. Width: about 20-33 mm. Apex: oval. Texture: Upper and under surface: smooth and satiny. Color (when fully opened): Upper side, dorsal: purple (RHS 72B) with purple stripes (RHS 72A) and white spots (RHS NN155C). Lateral: main color is purple (RHS N78C) with purple stripes (RHS 72A). At the base red/purple spots and stripes (RHS 59A and RHS 71A) and white spots (RHS NN155C) and a haze of yellow/green (RHS 145C). Under side, dorsal: red/purple (RHS 72B) with a haze of greyed/purple (RHS 183B) and yellow/green spots and stripes (RHS 145C). Lateral: red/purple (RHS 70A) with yellow/green spots and stripes (RHS 145C) and a greyed/purple haze (RHS 183B). Color (when first opened): purple (RHS 72B) with purple stripes (RHS 72A) and white spots (RHS NN155C) with a yellow/green haze (RHS 146D).

*Pedicel*.—Length: about 35 mm. Diameter: about 4 mm. Texture: glabrous and smooth. Color: starting at the flower red/purple (RHS 70B) which runs to red/purple (RHS 71B) with yellow/green stripes/spots (RHS 145C).

Reproductive organs:

*Arrangement*.—The stamens, style and stigmas are fused into a single, short structure called the column, possessing one terminal anther with pollen grains united into a pollinia, which are covered by an anther cap. The stigma is located under the column behind the pollinia. The ovary is inferior with three carpels present. The plant has not produced seed.

*Column*.—Length: about 5 mm. Diameter: about 5 mm. Color: white (RHS NN155D).

*Pollinia*.—Quantity: two. Diameter: about 3 mm. Color: yellow/orange (RHS 23A).

*Ovary*.—Length: about 4 mm. Diameter: about 3 mm. Color: white (RHS NN155D).

Disease/pest resistance/susceptibility: No specific resistance or susceptibility observed.

Temperature tolerance: Tolerant to a low temperature of about 15° C. and to a high temperature about 30° C.

What is claimed is:

1. A new and distinct *Phalaenopsis* plant named 'Elastic Love', as illustrated and described herein.

* * * * *